US008880146B1

(12) United States Patent
Schepkin et al.

(10) Patent No.: US 8,880,146 B1
(45) Date of Patent: Nov. 4, 2014

(54) TUMOR RESISTANCE AND SODIUM/DIFFUSION MRI

(71) Applicant: The Florida State University Research Foundation, Inc., Tallahassee, FL (US)

(72) Inventors: Victor D. Schepkin, Tallahassee, FL (US); Cathy W. Levenson, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 126 days.

(21) Appl. No.: 13/719,864

(22) Filed: Dec. 19, 2012

Related U.S. Application Data

(60) Provisional application No. 61/598,074, filed on Feb. 13, 2012, provisional application No. 61/579,813, filed on Dec. 23, 2011.

(51) Int. Cl.
  *A61B 5/055* (2006.01)
  *G06K 9/00* (2006.01)
  *G01R 33/48* (2006.01)
  *A61B 5/00* (2006.01)

(52) U.S. Cl.
  CPC .............. *G01R 33/48* (2013.01); *A61B 5/4839* (2013.01)
  USPC .......................................... 600/411; 382/131

(58) Field of Classification Search
  USPC ............ 600/410, 411; 382/128, 131; 324/307
  See application file for complete search history.

(56) References Cited

PUBLICATIONS

Schepkin, Victor et al. "Proton and sodium MRI assessment of emerging tumor chemotherpeutic resistance". NMR Biomed. Dec. 2006; 19(8): 1035-1042.*
R. Deberardinis, et al., The Biology of Cancer: Metabolic Reprogramming Fuels Cell Growth and Proliferation, Cell Metabolism 2008, vol. 7:p. 11-20.
M. Vander Heiden, Targeting cancer metabolism: a therapeutic window opens, Nature Reviews: Drug Discovery, 2011, vol. 10:p. 671-684.
A. Ramanathan, et al., Perturbational profiling of a cell-line model of tumorigenesis by using metabolic measurements, PNAS 2005, vol. 102, Issue 17:p. 5992-5997.
I. Silver, et al., Ion homeostasis in brain cells: differences in intracellular ion responses to energy limitation between cultured neurons and glial cells, Neuroscience, 1997, vol. 78, Issue 2:p. 589-601.
R. Gatenby, et al., Why do cancers have high aerobic glycolysis? , Nature Reviews: Cancer, 2004, vol. 4: p. 891-889.
C. Bortner, et al., Cell shrinkage and monovalent cation Fluxes: Role in apoptosis, Archives of Biochemistry Biophysics, 2007, vol. 462:p. 176-188.

* cited by examiner

*Primary Examiner* — Michael Rozanski
(74) *Attorney, Agent, or Firm* — Nilay J. Choksi; Smith & Hopen, P.A.

(57) ABSTRACT

The present invention enables a safe and noninvasive assessment of tumor resistance using one diffusion or sodium MRI scan over the entire tumor. The evaluation can be done before therapy and can help select a strategy of treatment. The invention can be used in different types of tumors in most parts of the human body. The level of tumor resistance can be determined reproducibly and quickly. The results can be used immediately to create individualized therapy. The invention allows clinicians to avoid ineffective therapies, which may be more harmful than useful, or come up with the other more appropriate alternatives.

12 Claims, 5 Drawing Sheets

TUMOR RESISTANCE AND SODIUM/DIFFUSION MRI

FEDERALLY SPONSORED RESEARCH OR DEVELOPMENT

This invention was made with Government support under Grant No. DMR-0654118 awarded by the National Science Foundation and Grant No. R21 CA119177 by the National Institute of Health. The government has certain rights in the invention.

BACKGROUND OF THE INVENTION

1. Field of the Invention

This invention relates, generally, to tumor resistance. More particularly, it relates to a noninvasive evaluation of tumor resistance using sodium and/or diffusion magnetic resonance imaging (MRI).

2. Description of the Prior Art

Tumor resistance is typically determined after a course of therapy, following an extended period of drug administration. It is well known that during tumor progression, especially after therapeutic interventions, the tumor may become more resistant to therapies; consequently, the tumor requires a much higher concentration of a chemotherapeutic drug to achieve the same level of response, or the chemotherapy may be rendered ineffective. Drug intervention itself can make a tumor even more resistant than the tumor was prior to drug intervention. Thus, it would be important to have the capability to evaluate tumor resistance promptly and noninvasively prior to drug therapy.

Currently, a biopsy is the conventional technology used to deliver information on tumor resistance prior to therapy. The procedure for biopsy is invasive, as tumor cells must be extracted. This is often a complicated procedure, and not all patients may agree to undergo it. Tumor cells must be extracted from biopsy tissue. Cells are then cultivated in the presence of a selected drug to determine the level of tumor cell resistance to that drug.

However, the biopsy process may take approximately four days to achieve the results desired regarding tumor resistance. There are also the added expenses of labor and equipment to perform the biopsy.

Moreover, handling any in vitro cancer cell can itself change the evaluated tumor resistance. Reproducibility and accuracy of in vitro assays are strongly dependent on multiple factors, including cancer cell aggregation, life span of the chemotherapeutic drug, tissue handling, and conditions of cell cultivation. Consequently, the results of evaluation may be only indicative but not quantitative.

Additionally, a biopsy is not always an acceptable option, for example in the case of brain tumors. Moreover, cells in one part of a tumor can have a different level of resistance compared to another region of the same tumor. Even taking multiple biopsy samples is unlikely to fully reveal the heterogeneous nature of large tumors.

Positron emission tomography (PET) is another option that has the potential for evaluating tumor cell resistance. It relies on cancer cell glycolytic metabolic activity. Currently, it is only expected that PET could be useful for diagnosis of tumor resistance. Disadvantages of such assays include administration of radioactive materials to patients and the cost of PET analyses. PET yields low-resolution images and must be combined with computer tomography to obtain any anatomical localization of the tumor. The results of PET are also strongly affected by multiple technical, biological and physical factors, thus creating the potential of inaccurate results.

Many cancers quickly develop mechanisms enabling them to evade chemotherapeutic interventions. The adaptive changes are inevitable during tumor development even after minor variations in environmental factors such as medication and diet. Large changes are especially evident after drug interventions. Thus, the typical therapy applied to the same type of tumor and at the same anatomical place may not be successful because of unavoidable mounting resistance. Reliable methods for determining drug resistance in advance of therapy do not yet exist.

Accordingly, what is needed is a prompt, noninvasive and individualized evaluation of tumor resistance. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for noninvasive, comprehensive and individualized evaluation of tumor resistance and treatment thereof is now met by a new, useful and nonobvious invention.

Certain embodiments of the present invention enable a safe and noninvasive assessment of tumor resistance using one diffusion or sodium MRI scan over the entire tumor. The evaluation can be performed prior to therapy and can help select a strategy of treatment. The invention can be used in the brain glioma model but is contemplated for use in different types of tumors in most parts of the human body. The level of tumor resistance can be determined reproducibly in a relatively short amount of time, for example less than thirty minutes, and the results can be used immediately to create individualized therapy. The invention allows clinicians to avoid ineffective therapies, which may be more harmful than useful or come up with the other more appropriate alternatives.

It is also contemplated that certain embodiments of the present invention can detect changes in tumor resistance that occur possibly because of alterations in the energy metabolism of cancer cells.

An embodiment of the invention can be effective for drug development as well. It can facilitate a separation of the effects due to metabolic changes in the tumor at the beginning of therapy from the effects introduced by drug intervention.

In an embodiment, the current invention comprises a method of noninvasively evaluating resistance of a tumor to a particular therapeutic drug prior to administration of the drug. The method includes conducting a sodium and/or diffusion MRI on a tumor of a subject and on a normal region of the subject—for example, the normal region in brain being contralateral to the tumor. When the images of the MRI procedures have been obtained, the indicias (i.e., sodium and/or diffusion) are measured and analyzed. These indicias are compared between the tumor region and normal region. A low level of the indicia in the tumor region, relative to the level of indicia in the normal region, indicates a higher/increased tumor resistance to the drug.

The tumor may be a glioma type, though tumors on any part of the body of the subject are contemplated.

The therapeutic drug may be carmustine, though chemotherapeutic drugs of any kind are contemplated.

The MRI may be performed using a back projection technique that allows for detection of a total in vivo sodium signal without magnetic resonance losses. Further, the images may be obtained with a short readout time to minimize partial volume effect due to quadrupolar interactions of sodium or due to multi-exponential relaxation of sodium in vivo.

The method may further include the step of conducting a partial volume correction of said analysis to alleviate lesion size changes of said tumor over time.

The method may further include the step of imparting the results of the analysis/comparison to a whole volume of the tumor, thereby providing an average of the tumor resistance and a spatial heterogeneity of the tumor resistance.

In a separate embodiment, the current invention comprises a method for evaluating the efficacy of an agent for the treatment of cancer in a subject. The method includes conducting sodium and/or diffusion MRI on a tumor of a subject and on a normal region of the subject—in the brain, the normal region can be contralateral to the tumor. When the images of the MRI procedures have been obtained, the indicias (i.e., sodium and/or diffusion) are measured and analyzed. These indicias are compared between the tumor region and normal region. A low level of the indicia in the tumor region, relative to the level of indicia in the normal region, indicates a higher/increased tumor resistance to the agent. Using this information, an effective amount of the agent is administered to the subject. Again, the tumor may be glioma and the agent may be carmustine, though other tumor types and agents are contemplated by the invention.

In a separate embodiment, the current invention comprises a method of detecting changes in resistance of a tumor to a therapeutic drug. The method includes conducting a first sodium and/or diffusion MRI on a tumor of a subject and on a normal region of the subject—in the brain, the normal region can be contralateral to the tumor. When the images of the MRI procedures have been obtained, the indicias (i.e., sodium and/or diffusion) are measured and analyzed. These indicias are compared between the tumor region and normal region to obtain a first value of tumor resistance. Thereupon, after a period of time, the method includes conducting a second sodium and/or diffusion MRI on a tumor of a subject and on a normal region of the subject—the normal region being contralateral to the tumor. When the images of the MRI procedures have been obtained, the indicias (i.e., sodium and/or diffusion) are measured and analyzed. These indicias are compared between the tumor region and normal region to obtain a second value of tumor resistance. The difference between the first and second values of tumor resistance is evaluated to determine the change in tumor resistance to the therapeutic drug. Again, the tumor may be glioma and the agent may be carmustine, though other tumor types and agents are contemplated by the invention.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1A:
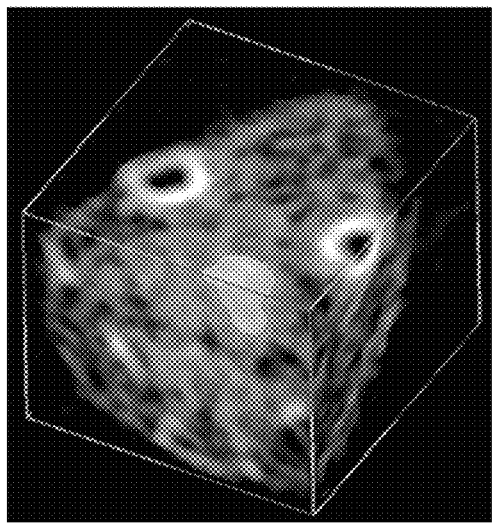
FIG. 1A depicts a three dimensional sodium MRI of a rat glioma at a resolution of 0.5×0.5×0.5 mm. Note an increased sodium concentration in glioma represented by high intensity area in rat brain.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

During cancer progression, many tumors develop evasive mechanisms permitting them to thwart chemotherapeutic interventions. Consequently, it is crucial to formulate individualized effective treatments promptly to provide a definitive and noninvasive assessment of tumor resistance. Mitochondria play a central role in cellular energy metabolism, apoptosis and maintenance of ion gradients. The function of mitochondria is closely associated with the mechanism of tumor resistance (R. DeBerardinis, et al., Cell Metabolism 2008, 7:p11; M. Vander Heiden, Nature Reviews, Drug Discovery 2011, 10:p671; A. Ramanathan, et al., PNAS 2005, 102(17):p5992; I. Silver, et al., Neuroscience 1997, 78:p589; R. Gatenby, et al., Nature Reviews 2004, 4:p891; C. Bortner, Arch Biochem Biophys 2007, 462:p176). As such, a shift in energy metabolism due to increased tumor resistance may affect sodium homeostasis, as taught by the current invention.

The present invention enables various methodologies for tumor resistance assays, more specifically using the noninvasive capability of sodium and/or diffusion MRI to determine tumor resistance. Measurement of sodium concentration and/or the apparent diffusion coefficient (ADC) is performed in the tumor and surrounding (or contralateral) normal tissue. The sodium concentration and/or ADC are compared between the tumor and the contralateral normal tissue. The results of this comparison reveal tumor resistance for a particular chemotherapeutic drug, and the measurements are recommended for the whole tumor volume.

The inventive concept contemplated by the current invention comprises the ability to perform a sodium MRI and/or diffusion MRI and accurately and noninvasively ascertain the resistance of a tumor to a particular chemotherapeutic drug. Further included is determining the tumor resistance by comparing sodium and/or diffusion in the tumor region of a subject and comparing those values to the intracellular sodium and/or diffusion found in a normal region of the subject, wherein the normal region is adjacent or contralateral to the tumor region. By making this comparison, the level of increase of sodium/diffusion in the tumor region from the normal region determines how resistant the tumor is to the particular chemotherapeutic drug.

Among sodium MRI and diffusion MRI, sodium MRI tends to be more sensitive to changes in tumor resistivity. Sodium MRI is becoming more accessible as higher field MRI scanners are utilized in hospitals and clinics. The initial image analysis in both cases can be performed by any known image processing software. The partial volume effect for sodium and diffusion MRI, however, must be corrected according to the suggested model since tumor lesion size changes over time and to take into account a possible range of MRI spatial resolution used during measurements.

Sodium MRI can be performed using the back projection technique, which in turn allows for detection of a total in vivo sodium signal without MR losses. Each voxel value of the tumor lesion can be used for the evaluation of tumor resistance and its heterogeneity. Thus, the average resistance and spatial heterogeneity of tumor resistance can be determined at the same time.

Figure 3:
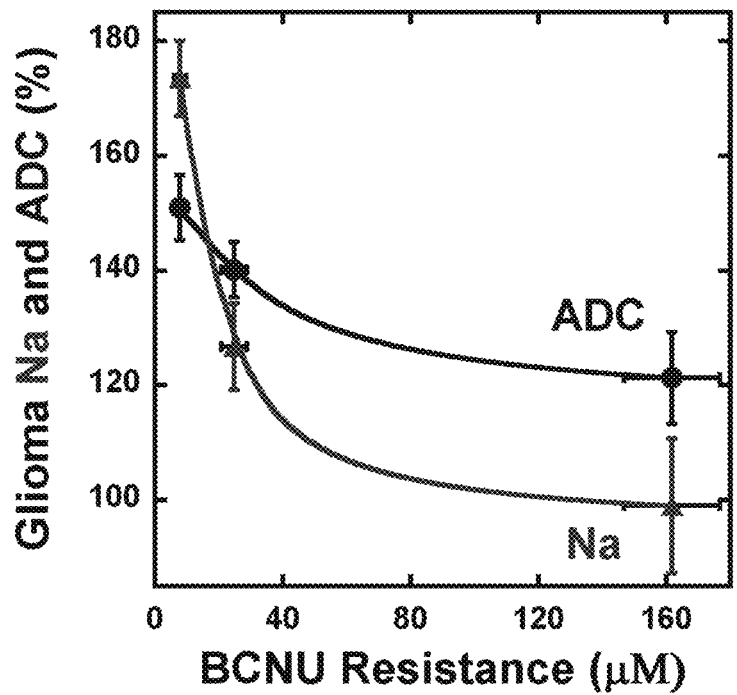
FIG. 3 depicts a relationship of in vivo sodium concentration and diffusion in untreated rat glioma (in percentage relative to normal brain) with its tumor cell carmustine resistance.
Figure 6:
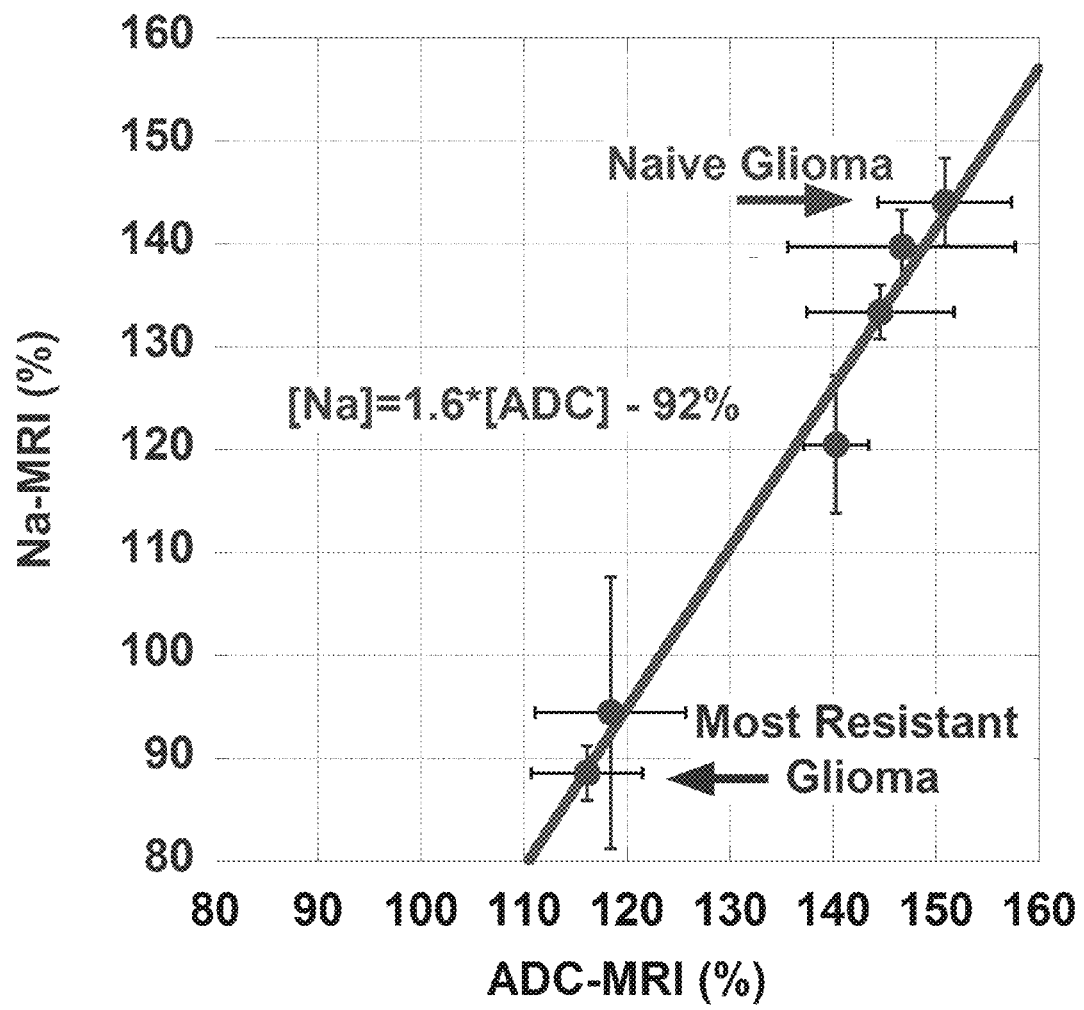
FIG. 6 depicts the correlation of sodium concentration and diffusion in untreated rat glioma for a range of glioma resistance to carmustine. Sodium and diffusion are presented in percent relative to the normal brain values of 45 mM (8) and $0.78×10^{-3}$ mm$^2$/s (9), respectively.

Sodium or diffusion MRI may be used independently to provide evidence of tumor resistance changes. However, as depicted in FIG. 3 and FIG. 6, sodium MRI is more sensitive to the alteration in tumor resistance relative to diffusion MRI.

Additionally, embodiments of the present invention determine tumor responses prior to therapy. The mechanism of the relationship between MRI methods and tumor resistance is based on the capability of sodium MRI to reflect changes in cell ion homeostasis and by this way to detect changes in the energy metabolism of cancer cells.

The present invention can use sodium and/or diffusion MRI in order to examine the alteration in tumor cell resistance due to the relationship between tumor diffusion and tumor resistance. This correlation of sodium MRI with diffusion MRI can be an indirect reflection of the changes in sodium ion homeostasis. This association can be a result of an in vivo relationship that water fluxes typically follow the corresponding sodium ion fluxes.

The relative difference between sodium/diffusion MRI in a tumor and normal tissue represents a shift of the metabolic energy status in tumor cells. In naïve tumors, due to multiple factors, including increased intracellular sodium concentration in tumors and lower density (i.e., more loosely packed) tumor cells (e.g., in glioma), higher sodium content (in sodium MRI) and diffusion (in diffusion MRI) are typically observed. The present invention shows that the decreased intracellular sodium concentration and decreased diffusion detected by MRI correlate with increased tumor resistance. The closer diffusion and sodium concentrations in a tumor lesion are to normal values, the more resistant a tumor is. Extreme resistance is characterized by a minor difference of sodium MRI in the tumor lesion relative to normal tissue (e.g., contralateral to said tumor). Such changes in MRI signals represent absence of metabolic energy deficit in tumor cells, thereby helping the tumor cells resist antitumor therapeutic interventions. Thus, an increased resistance of the tumor cell detected by MRI is an indication of tumor cell energy status, and such marker can be relevant to a broad spectrum of anticancer drugs.

Figure 2:
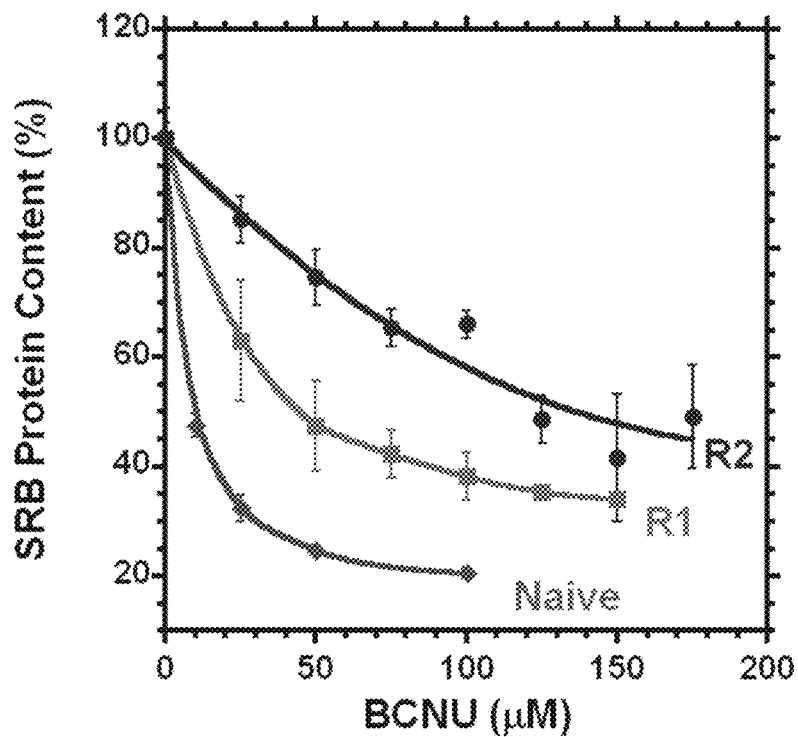
FIG. 2 depicts sulfarodamine blue assays of 9L glioma cell resistance to carmustine (BCNU). Curve R2 represents the most resistant glioma cells.

As an option, a calibration curve depicting such changes in MRI signals can be established for every tumor type and anticancer drug. Calibration curves can provide quantitative measures for the alterations in tumor resistance for a specific drug. Illustrations of certain curves are given in FIGS. 2 and 3. FIG. 2 demonstrates a difference in resistance for three cancer cell lines with a wide range of resistance to carmustine, which were used for tumor implantation. In FIG. 2, the cell lines R1 and R2 can be seen to have increased resistance to 1,3 bis(2-chloroethyl)-1-nitrosurea (BCNU, carmustine). FIG. 3 demonstrates the corresponding values of sodium and diffusion MRI in vivo, in a rat glioma model for tumors from naïve and resistant cell lines R1 and R2. In FIG. 3 and FIG. 6, an enhanced sensitivity of sodium MRI to changes in tumor resistance can be seen.

Figure 4A:
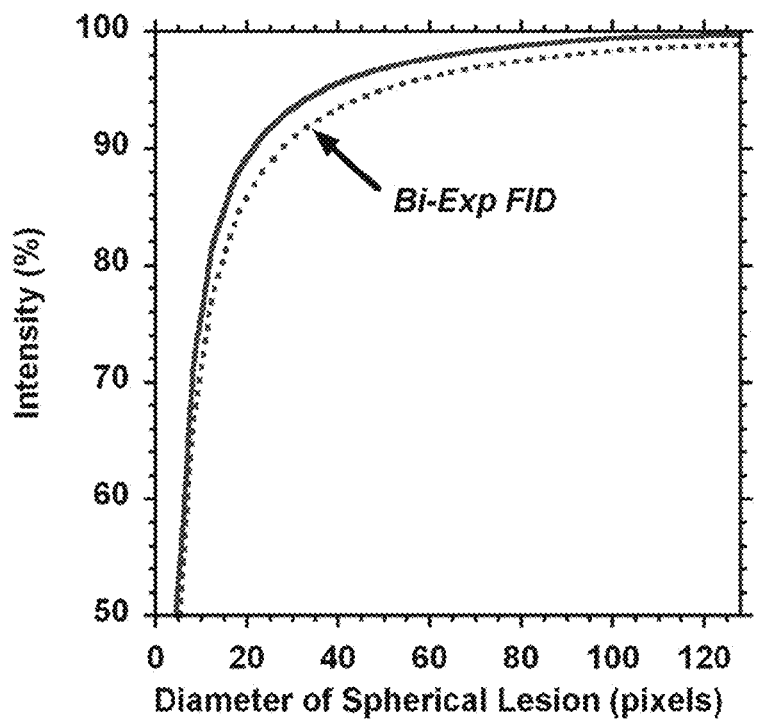
FIG. 4A depicts a 3D model of partial volume effect on sodium or diffusion MRI intensity measurements for any field of view in relation to the diameter of the tumor lesion expressed in pixels, according to an embodiment of the present invention. The broken line demonstrates the additional effect on sodium MRI intensity stemming from the presence of sodium quadrupolar interactions in vivo.
Figure 4B:
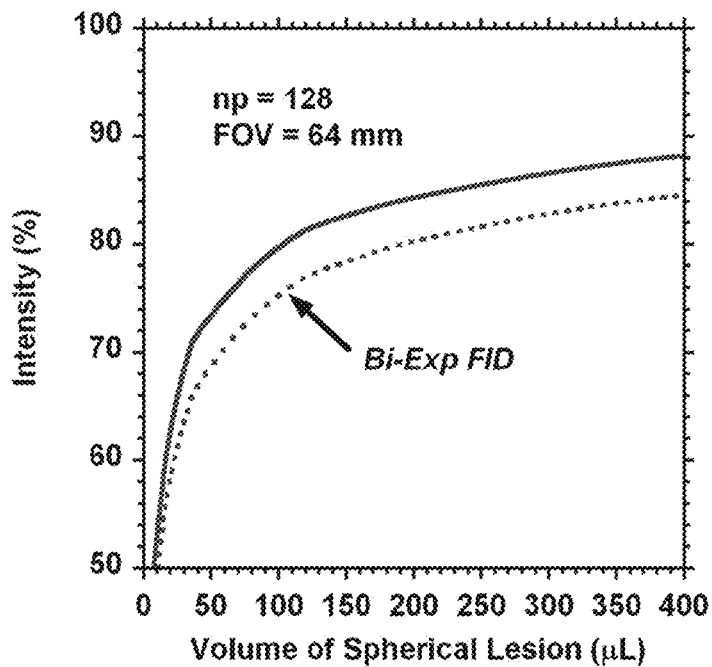
FIG. 4B depicts an example of a 3D model of partial volume effect on sodium or diffusion MRI intensity measurements for the specific field of view in relation to the volume of the tumor lesion, according to an embodiment of the present invention. The broken line demonstrates the additional effect on sodium MRI intensity stemming from the presence of sodium quadrupolar interactions in vivo.

The tumor lesion intensity data for sodium and diffusion MR images can be corrected for the 3D partial volume effect using the model embodiments of this invention. As depicted in FIGS. 4A and 4B, the models include corrections for the limited resolution of sodium and diffusion MRI and illustrate the need of additional corrections in the presence of quadrupolar interaction of sodium in vivo. Lesions in the model had spherical size with a diameter presented by pixel number (x-axis). The shape of a lesion in the model can be selected from sodium or diffusion MRI to represent a real shape of the tumor.

In FIG. 4A, the average MR signal intensity (y-axis) in the lesion is given relative to the lesion reference with any size of field of view (FOV) covered by matrix of 128×128×128. FIG. 4B depicts an example of the PV effect for the range of tumor volumes detected. FIGS. 4A and 4B both depict PV effect for the MRI intensity of lesion relative to the surrounding area.

The dotted lines present a possible additional contribution that may occur due to the bi-exponential decay of the free induction decay (FID) during readout time of 2 ms. The last effect can be more dramatic if the imaging readout time is larger than 2 ms.

Sodium MRI images can be acquired with a short readout time to minimize partial volume effect due to quadrupolar interactions of sodium or due to multi-exponential relaxation of sodium in vivo. The real tumor has a non-spherical size. However, the tumor volume determined by MRI, for example from diffusion or even sodium MRI, can be used according to FIGS. 4A and 4B to give the best estimation of the partial volume effects. Though the dependence between tumor resistance and MRI data can be seen without partial volume corrections, PV correction will give more accurate and precise values of sodium and diffusion, independent of tumor volumes.

Example 1

Figure 1B:
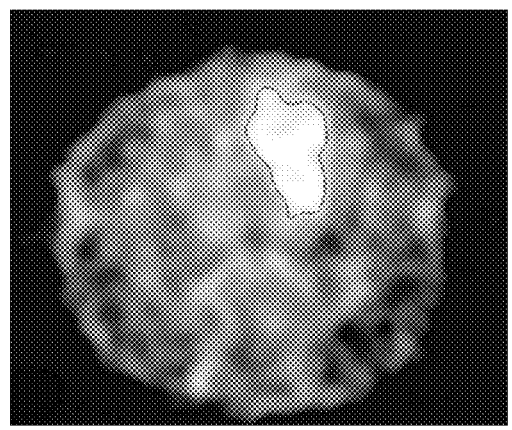
FIG. 1B depicts a sodium MRI slice selected through the central part of a rat glioma. Note a heterogeneity of increased sodium concentration inside glioma.
Figure 1C:
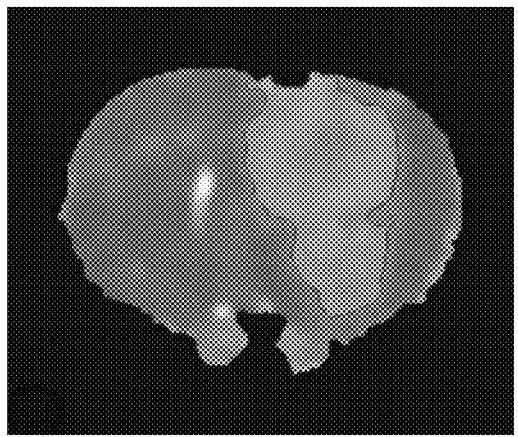
FIG. 1C depicts an apparent diffusion coefficient (ADC) map for a sodium MRI slice selected through the central part of a rat glioma. The increased diffusion inside glioma is seen as a high intensity area in the right part of rat brain.

A study was performed using ultra-short echo time for a sodium MRI to detect total sodium concentration in tumors. A high resolution sodium MRI, as depicted in FIGS. 1A and 1B, and diffusion MRI, as depicted in FIG. 1C, were achieved using a high magnetic field of about 21.1T (National High Magnetic Field Laboratory, Tallahassee, Fla.). A two-dimensional view of a slice of the sodium MRI is depicted in FIG. 1B. The slice was made through a central part of the rat glioma. A corresponding ADC map for the sodium slice, as depicted in FIG. 1B, is depicted in FIG. 1C and demonstrates the increased sodium content and diffusion values in the tumor relative to the surrounding normal brain. The areas of the glioma were selected by contour line.

A. Materials and Methods

Three sub-clones of 9L gliosarcoma cells with different resistance to BCNU were selected by using the In Vitro Toxicology Assay Kit (Sigma-Aldrich TOX-6) based on the sulforhodamine blue (SRB) method. Cell viabilities were determined after cells were exposed for 72 hours to media having a range of BCNU concentrations, as seen in FIG. 2. The naïve and resistant cells were implanted intra-cranially in three groups of male Fisher 344 rates (n=5 in each group, weight ≈150 g). At about 11 days after tumor implantation, tumor sodium, diffusion and tumor volume were detected.

The experiments were performed on a 21.1T MRI scanner using proton (900 MHz) and sodium (237 MHz) signals, Bruker Advance III console equipped with 64 mm gradient coil (RR Inc.), and GREAT60 amplifiers. The experiments were monitored and operated by Paravision v5.1 software.

Sodium was detected by 3D back-projection MRI with short echo time (TE) of 0.1 ms. The short readout time of about 2 ms minimized the partial volume effect of bi-exponential FID of sodium signals. To avoid saturation, a long repetition time TR was selected (100 ms). Sodium MRI scans had a duration period of about 27 minutes and resolution of 0.5×0.5×0.5 mm.

Diffusion SE pulse sequence had flow/motion-compensated shape for diffusion gradients, two b values of 100 and 1000 sec/mm$^2$, TE of 34 ms and 15 slices. The back-projection acquisition allowed for additional motion compensation during image processing. The double tuned sodium/proton RF probe was used for in vivo rat MR imaging at 21.1T, thereby allowing the sodium and diffusion MRI to be performed without animal repositioning.

All animal experiments were conducted according to protocols approved by The Florida State University Animal Care and Use Committee.

B. Results and Discussion

As depicted in FIG. 2, naïve 9L cells were seen to be more susceptible to BCNU presence than resistant cells. Naïve 9L cells displayed a population decrease of 2.7 times during cultivation with 7.8 µM of BCNU. For the resistant sub-cultures, the corresponding BCNU resistance values were 24.7 µM (R1) and 161.7 µM (R2). All cell lines initiated gliomas in vivo with doubling times of approximately 2.5 days.

As depicted in FIG. 3, about 11 days after tumor implantation, sodium concentration in the tumors from naïve cells was 173% of a normal contra-lateral brain. The glioma formed from the resistant cell lines had lesser sodium concentrations of 127% (R1) and 99% (R2). The corresponding values of diffusion were 151% in naïve glioma and 140% (R1) and 121% (R2). The values are given relative to a normal brain. All observed differences for sodium and diffusion are statistically significant ($p<0.05$).

Tumor sodium concentration is mainly determined by the efficiency of the Na/K pump and in this way can reflect the available cellular level of ATP. Resistant tumor cells may have an increased glucose transport and glycolysis, which leads to increased ATP production. The increased ATP production is capable of compensating for the ATP deficit that naïve tumors may experience. The enhanced sensitivity of sodium MRI has been demonstrated to be able to detect small variations in glioma cell drug resistance to therapy.

Changes in tumor resistance can be detected by sodium and diffusion MRI. The relationship between resistance and sodium/diffusion MRI correlate with the shift in energy metabolism that can be observed in tumors (Warburg effect), which can be further intensified in resistant tumors. Using embodiments of the current invention, alterations in tumor resistance can be assessed prior to treatment, allowing individualized adjustments of the therapy to prevent ineffective treatments.

Example 2

Energy metabolism in tumors is different from normal cells and it is a promising target in the treatment of cancer (DeBerardinis, R. et al. Cell Metabolism 2008, 7:p11; Vander Heiden, M. Nature Reviews, Drug Discovery 2011, 10:p671; Ramanathan A. et al. PNAS 2005, 102(17):p5992; Silver, I. et al. Neuroscience 1997, 78:p589; Gatenby, R. et al. Nature Reviews 2004, 4:p891; Bortner, C. Arch Biochem Biophys 2007, 462:p176). Tumors generally have higher sodium concentration than normal tissue; the sodium concentration can be detected by sodium MRI. Sodium concentration in glioma is not the same and its variation shows a remarkable correlation with glioma drug resistance (Schepkin, V D. et al. Proceedings of ISMRM, Melbourne, Australia, 2012, p. 184). Through the current experiment, it was thought that increased tumor resistance is determined by the energy metabolism shift that can be detected by a corresponding shift in sodium homeostasis. Diffusion may also follow the corresponding changes in glioma and has the potential to convey alterations in tumor resistance using the strong MR signal from protons. Thus, MRI has the potential to reflect tumor resistance and changes in tumor drug resistance noninvasively.

A. Materials and Methods

Six 9L gliosarcoma cell lines with a range of resistance to 1,3 bis(2-chloroethyl)-1-nitrosurea (BCNU, carmustine) were created. In four lines, the naïve glioma cells were subjected to a range of BCNU concentration up to 150 µM during their cultivation. Additionally, the two most resistant cell lines were prepared the same way but started from glioma cells extracted from the tumor after the animal was subjected to BCNU therapy. Glioma cell line resistance to BCNU was determined shortly before intracranial implantation by growing the cells for 72 hours in media having an array of BCNU concentrations and assessing the number of viable cells through protein detection by sulforhodamine blue (using the In Vitro Toxicology Assay Kit Sigma-Aldrich TOX-6). Six groups of male Fisher 344 rats (n=4-6 in each group, weight ~150 g) were implanted with the cells, and after ~11 days, tumor sodium and diffusion were evaluated. The experiments were performed on a 21.1T MRI scanner (Bruker Avance III console equipped with 64 mm gradient coil (RR Inc) and operated by Paravison V5.1 software) using proton (900 MHz) and sodium (237 MHz) signals. Sodium was detected by 3D back-projection MRI with ultra-short echo time of TE=0.1 ms. The short readout time of ~2 ms was selected to minimize the partial volume effect from bi-exponential FID of sodium signals. Sodium MRI scans had TR of 100 ms to reduce MR saturation and resolution of 0.5×0.5×0.5 mm (scan time=27 min). The diffusion SE pulse sequence had flow/motion compensated diffusion gradients with two b values of 100 and 1000 (s/mm2), TE=34 ms and 15 slices. Here, the back-projection acquisition mode allowed for additional motion compensation. Sodium and diffusion MRI scans were performed without repositioning on animals by using the double tuned sodium/proton RF probe.

All animal experiments were conducted according to the protocols approved by the Florida State University ACUC.

B. Results and Discussion

Figure 5A:
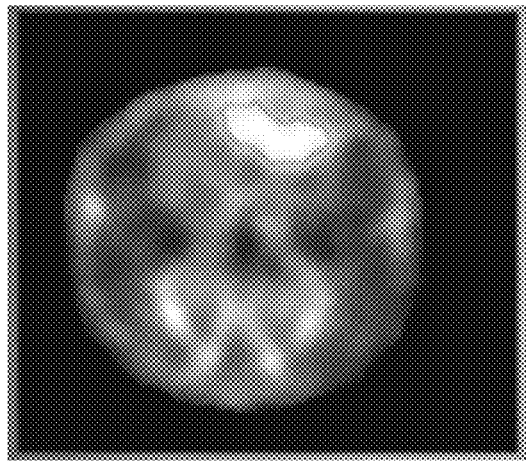
FIG. 5A is a sodium MRI of non-treated rat glioma originated from 9L cells having low carmustine resistances (resolution is 0.5×0.5×0.5 mm). Note a high sodium concentration inside the tumor area.
Figure 5B:
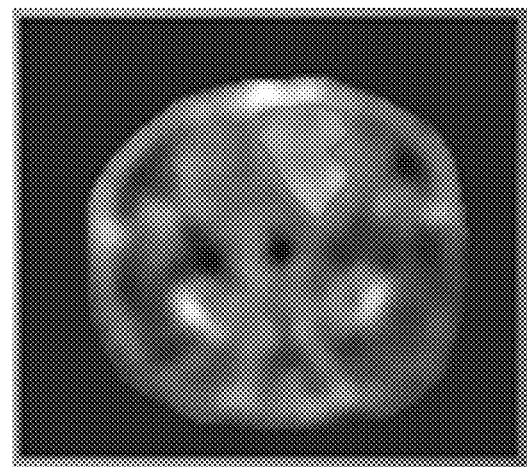
FIG. 5B is a sodium MRI of non-treated rat glioma originated from 9L cells having high carmustine resistances (resolution is 0.5×0.5×0.5 mm). Note a low sodium concentration inside the tumor area.

The naïve and resistant 9L cells yielded different brain tumors. The difference is very noticeable from sodium MRI without additional processing, as depicted in FIGS. 1A and 1B. Tumors from naïve 9L cells have a high tumor sodium concentration relative to the normal brain, while tumors from resistant glioma cells show a very low sodium contrast pattern, as seen in FIGS. 5A-5B. Sodium concentration in glioma has a strong correlation (R=0.99) with diffusion in glioma for a wide range of the glioma resistance, as depicted in FIG. 6. Resistance of the naïve glioma to carmustine was 21.8±1.3 µM, while the most resistant glioma cell line had resistance of 163±23 µM. Sodium has an almost doubled sensitivity to the changes in resistance relative to diffusion, seen in FIG. 6. The most resistant glioma has the lowest tumor sodium concentration and the lowest diffusion values.

Regarding whether sodium in tumors can be related to energy metabolism in cancer cells, it is known that the Na/K pump is the major extrusion mechanism of sodium out of the intracellular space, and it may consume up to ~60% of total ATP to perform this task. The increased intracellular Na content can lead to an additional activation of the Na/K pump and to a higher consumption rate of ATP. Thus, increased sodium can be an indicia of energy deficit in cancer cells and be detectable by MRI.

Naïve (i.e., less resistant) cells have the largest deficit of energy and such cells are the most vulnerable to therapeutic interventions. The absence of an energy deficit in resistant tumor cells is an advantage to such cells in their resistance against drug interventions.

The results of this experiment demonstrated that emerging tumor resistance can be detected by sodium and diffusion MRI. The evaluation can be done noninvasively and prior to therapy.

Application

It is important to note that the present invention contemplates more than glioma resistance to carmustine, as it is the change in sodium levels (i.e., change in energy metabolism) within tumors that determines its resistance, rather than the chemotherapeutic drug itself. Further, the invention contemplates various types of tumors/cancers, as increased intracellular sodium levels are seen in all typical tumors. Thus, the current invention contemplates more than carmustine and glioma, as the enabled mechanism can be used broadly to evaluate resistance of any particular tumor to any particular chemotherapeutic drug.

An energy-based MRI indicia of tumor resistance can be predictive for a range of different therapeutic interventions. The prompt evaluation of tumor resistance may help to formulate individual treatment and avoid unsuccessful therapies.

DEFINITION OF CLAIM TERMS

Carmustine: This term is used herein to refer to an example of a chemotherapeutic agent. The current invention contemplates the current methodology being effective for any chemotherapeutic agent, as the methodology lies in levels of intracellular sodium and diffusion within the tumor and normal regions, regardless of drug used.

Contralateral: This term is used herein to refer to the spatial arrangement between the normal region of a subject and the tumor region of that subject, wherein the regions are opposite from one another relative to the body or the subject, or portion thereof.

Diffusion MRI: This term is used herein to refer to a type of MRI method that depicts the movement of molecules within the body, or portion thereof, under imaging.

Diffusion: This term is used herein to refer to the movement of molecules within a subject's tumor region or normal region, or portions thereof, under imaging.

Glioma: This term is used herein to refer to a type of tumor that arises from glial cells in the brain or spinal cord.

Indicia: This term is used herein to refer to indications within an imaged body. Indicia may be intracellular sodium, diffusion, etc. The level or concentration of the indicia reveals the resistance of the tumor to a particular therapy.

Intracellular sodium: This term is used herein to refer to the level or concentration of sodium within a subject's tumor region or normal region, or portions thereof, under imaging.

Level of indicia: This term is used herein to refer to concentration of sodium or diffusion, thereby providing an indication of tumor resistance when level of indicia in a subject's tumor region is compared to the level of indicia in that subject's normal region.

MRI: This term is used herein to refer to a medical imaging technique used in radiology to visualize the internal structures of the body of a patient or subject, or portion thereof. Various types of MRI procedures are known, for example sodium MRI and diffusion MRI that can detect the ionic gradient state or water diffusive mobility of the structure subject to the MRI.

Noninvasive: This term is used herein to refer to the ability to perform a medical procedure without requiring incision to be made into a patient or subject, or a portion thereof. In the conventional art, evaluation of tumor resistance is typically performed through a biopsy, which is an invasive procedure. Contrastingly, the current invention evaluates tumor resistance noninvasively.

Normal region: This term is used herein to refer to the portion of the body of the patient or subject or MRI test sample that is adjacent or contralateral to the tumor region of that patient or subject.

Resistance: This term is used herein to refer to the reduction in effectiveness of a therapy, for example, as seen in the current invention, an increased concentration of chemotherapeutic drug needed to achieve the same result.

Sodium MRI: This term is used herein to refer to a type of MRI method that depicts the intracellular sodium content of the body, or portion thereof, under imaging. It may also include MRI of other ions, for example potassium and chlorine. Their intracellular gradients can also convey energy status of the cells. However, the current strength of magnetic fields used for MRI does not allow using such ions routinely, though use of such ions is contemplated by the current invention.

Subject: This term is used herein to refer to an individual or entity on which the current methodology is noninvasively performed.

Therapeutic drug: This term is used herein to refer to a substance used to treat an illness, relieve a symptom, or modify a chemical process in the body for a specific purpose. For example, as used in the current invention, a therapeutic drug may be used to reduce the size of a tumor or relieve the symptoms thereof.

Tumor region: This term is used herein to refer to the portion of the body of the patient or subject that has formed the abnormal growth.

Tumor: This term is used herein to refer to an abnormal growth of tissue formed naturally or artificially on a patient or subject.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of noninvasively evaluating resistance of a tumor to a therapeutic drug prior to any administration of said drug in order to detect changes in said resistance of said tumor to said drug prior to tumor therapy, comprising the steps of:
    conducting an MRI covering a tumor region and a normal region of a subject, said MRI selected from the group consisting of a sodium MRI, a diffusion MRI, and a combination thereof, said normal region located contralateral to said tumor region on said subject;
    selecting first image areas resulting from said MRI on said tumor region;
    selecting second image areas resulting from said MRI on said normal region;
    analyzing a level of indicias in said tumor region and a level of said indicias in said normal region, said indicias selected from the group consisting of sodium, diffusion, and a combination thereof; and
    determining said resistance of said tumor based on said analysis of said first image areas and said second image areas,
    whereby a low level of indicias in said tumor region relative to the level of said indicias in said normal region indicates increased tumor resistance to said therapeutic drug prior to said tumor therapy or any administration of said therapeutic drug.

2. A method as in claim 1, further comprising:
    said tumor being a glioma.

3. A method as in claim 1, further comprising:
    said therapeutic drug being carmustine.

4. A method as in claim 1, further comprising:
    said MRI performed using a back projection technique that allows for detection of a total in vivo sodium signal without magnetic resonance losses and without motion artifacts.

5. A method as in claim 4, wherein:
    obtaining said first image areas and obtaining said second image areas are performed by obtaining images with a short readout time to minimize partial volume effect due to quadrupolar interactions of sodium or due to multi-exponential relaxation of sodium in vivo.

6. A method as in claim 1, further comprising the step of:
    conducting a partial volume correction of said analysis to alleviate lesion size changes of said tumor over time.

7. A method as in claim 1, further comprising the step of:
    imparting results of said analysis to a whole volume of said tumor, thereby providing an average of said resistance and a spatial heterogeneity of said resistance of said tumor.

8. A method for predicting and correcting the efficacy of an agent for the treatment of cancer in a subject prior to any administration of said agent in order to detect changes in a resistance of a tumor to said agent prior to tumor therapy, comprising the steps of:
    conducting an MRI on a tumor region and a normal region of a subject, said MRI selected from the group consisting of a sodium MRI, a diffusion MRI, and a combination thereof, said normal region located contralateral to said tumor region on said subject;
    selecting first image areas resulting from said MRI on said tumor region;
    selecting second image areas resulting from said MRI on said normal region;
    analyzing a level of indicias in said tumor region and a level of said indicias in said normal region, said indicias selected from the group consisting of intracellular sodium, diffusion, and a combination thereof;
    determining tumor resistance based on said analysis of said first image areas and said second image areas, whereby a low level of indicias in said tumor region relative to the level of said indicias in said normal region indicates increased tumor resistance to said agent prior to said tumor therapy or any administration of said agent; and
    administering an effective amount of said agent to said subject according to said determination of said tumor resistance.

9. A method as in claim 8, further comprising:
    said tumor region containing glioma.

10. A method as in claim 8, further comprising:
    said agent containing carmustine.

11. A method of detecting changes in resistance of a tumor to a therapeutic drug during tumor progression prior to any administration of said drug in order to detect changes in said resistance of said tumor to said therapeutic drug prior to tumor therapy, comprising the steps of:
    conducting a first MRI on a tumor region and a normal region of a subject at a first time period, said first MRI selected from the group consisting of a sodium MRI, a diffusion MRI, and a combination thereof, said normal region located contralateral to said tumor region on said subject;
    analyzing a level of indicias in said tumor region and a level of said indicias in said normal region at said first time period, said indicias of said first time period selected from the group consisting of sodium, diffusion, and a combination thereof; and determining a first value of tumor resistance based on said analysis of said levels of indicias of said first time period, conducting a second MRI on said tumor region and said normal region of said subject at a second time period, said second MRI selected from the group consisting of a sodium MRI, a diffusion MRI, and a combination thereof, said normal region located contralateral to said tumor region on said subject;

analyzing a level of indicias in said tumor region and a level of said indicias in said normal region at said second time period, said indicias of said second time period selected from the group consisting of intracellular sodium, diffusion, and a combination thereof; and determining a second value of tumor resistance based on said analysis of said levels of indicias of said second time period; and evaluating the difference between said first value and said second value to determine the change in said resistance of said tumor to said therapeutic drug during progression of said tumor prior to said tumor therapy or any administration of said therapeutic drug.

12. A method as in claim 11, further comprising:
said tumor region containing glioma.

* * * * *